United States Patent
Jia (12)

(10) Patent No.: US 6,326,417 B1
(45) Date of Patent: Dec. 4, 2001

(54) ANTI-MICROBIAL DENTAL COMPOSITIONS AND METHOD

(75) Inventor: Weitao Jia, Wallingford, CT (US)

(73) Assignee: Jeneric/Pentron Incorporated, Wallingford, CT (US)

( * ) Notice: Subject to any disclaimer, the term of this patent is extended or adjusted under 35 U.S.C. 154(b) by 0 days.

(21) Appl. No.: 09/422,783

(22) Filed: Oct. 21, 1999

(51) Int. Cl.⁷ ...................................................... A61K 6/08
(52) U.S. Cl. ........................ 523/116; 523/118; 523/122; 433/228.1
(58) Field of Search ...................................... 523/115, 116, 523/117, 118, 122; 433/228.1

(56) References Cited

U.S. PATENT DOCUMENTS

| | | | |
|---|---|---|---|
| 3,066,112 | 11/1962 | Bowen | 65/261 |
| 3,194,784 | 7/1965 | Bowen | 523/116 |
| 3,751,399 | 8/1973 | Lee et al. | 106/35 |
| 3,882,858 | 5/1975 | Klemm | 606/76 |
| 3,925,895 | 12/1975 | Kliment et al. | 433/224 |
| 3,926,906 | 12/1975 | Lee, II et al. | 523/116 |
| 4,544,359 | 10/1985 | Waknine | 523/115 |
| 4,547,531 | 10/1985 | Waknine | 523/116 |
| 4,659,751 | 4/1987 | Bowen | 523/116 |
| 4,883,534 | 11/1989 | Sandham et al. | 106/35 |
| 4,939,132 | 7/1990 | Coburn et al. | 424/52 |
| 5,213,615 | 5/1993 | Michl | 106/35 |
| 5,218,070 | 6/1993 | Blackwell | 523/113 |
| 5,276,068 | 1/1994 | Waknine | 522/28 |
| 5,340,850 | 8/1994 | Shimasue | 523/115 |
| 5,348,475 | 9/1994 | Waknine et al. | 433/215 |
| 5,348,988 | 9/1994 | Suh et al. | 523/118 |
| 5,362,796 | 11/1994 | Tseng et al. | 524/548 |
| 5,385,728 | 1/1995 | Suh | 424/54 |
| 5,408,022 | 4/1995 | Imazato et al. | 526/258 |
| 5,576,652 | 11/1996 | Gaffar et al. | 433/173 |
| 5,733,949 | 3/1998 | Imazato et al. | 523/109 |

*Primary Examiner*—Peter Szekely
(74) *Attorney, Agent, or Firm*—Cantor Colburn LLP

(57) ABSTRACT

An anti-microbial dental restorative composition and method of use of the same for use in restoring the function and anatomy of a tooth. Dental restorative materials include bonding agents, resin cements and resin comprise polymerizable unsaturated monomers, oligomers, prepolymers with or without acid groups or combinations thereof. The anti-microbial dental composition prevents secondary decay, greatly enhances sustained anti-microbial activity for a longer period of time with minimum harm to the living structure and surrounding tissues and without affecting the composition's restorative properties.

52 Claims, No Drawings ical compositions are disclosed, for example, in
ANTI-MICROBIAL DENTAL COMPOSITIONS AND METHOD

BACKGROUND OF THE INVENTION

1. Field of the Invention

This invention relates to anti-microbial dental restorative compositions and a method of manufacture thereof. In particular, this invention relates to anti-microbial dental restorative compositions comprising salicylic acid, 4-amino salicylic acid, esters of salicylic acid, esters of 4-aminosalicylic acid, or sulfanilamide.

2. Brief Discussion of the Related Art

Dental restorative compositions include dental primers, adhesives, liners, filling materials, sealants, and luting cements, among others. Dental restorative compositions generally comprise at least one polymerizable monomer or prepolymer and a polymerization initiation system. Preferred polymerizable monomers or prepolymers are ethylenically unsaturated, and even more preferably acrylic and methacrylic resinous materials, with or without an acid moiety. Such compositions are disclosed, for example, in U.S. Pat. Nos. 3,066,142, 3,179,784, 3,751,399, 3,926,906, 4,544,359, 4,659,751, 5,218,070, 5,276,068, 5,348,475, and 5,348,988, which are incorporated by reference herein.

Dental restorative compositions are used to restore function and anatomy of a tooth both in human and animals either temporarily or permanently. During restoration of the tooth, bacterial species can enter the tooth, causing secondary decay. Additionally, if the residue of primary decay is not completely removed during restorative treatment, secondary decay of the tooth may continue underneath the site of restoration.

Incorporation of anti-microbial agents into certain dental compositions is known. For example, U.S. Pat. No. 3,925,895 to Kliment et al., discloses a hydrophilic polymerizable acrylate or methacrylate root canal filling material. Kliment discloses that various medicaments can be incorporated into the polymerizable monomer, such as Novocaine (procaine hydrochloride), Benzocaine (ethyl aminobenzoate), ascorbic acid, butacaine sulfate, dibucaine hydrochloride, Bacitracin, hexachlorophene, lincomycin hydrochloride, p-amino salicylic acid, sulfadiazine, procaine penicillin, aureomycin, streptomycin, tetramycin, chloramphenicol, penicillin, neomycin sulfate, succinoyl-sulfathiazole, cetyl pyridinium chloride, trimethyl benzyl ammonium chloride, triethyl dodecyl ammonium bromide, sulfathiazole, sulfanilamide, phenobarbital, pentabarbital sodium, butabarbital, diethyl stilbestrol, tetracycline, and xylocaine. While useful as root canal sealing materials, such swellable hydrophilic compositions are not themselves useful as dental primers, adhesives, liners, sealants, or cavity filling materials.

U.S. Pat. No 5,385,728 to Suh discloses a dental etching gel containing the quaternary ammonium compound benzalkonium chloride. One drawback of quaternary ammonium compounds is that their effectiveness is decreased in the presence of calcium or magnesium ions, or such as dental gauze. Another more serious drawback is that rather they can support the growth of some bacterial species belonging to the genus Pseudomonas.

Fluoride is used in dental restorative compositions as an antimicrobial agent to kill the bacteria and prevent secondary decay. Fluoride exhibits bactericidal activity when released from silicate cement continuously. However, the release of fluoride from the dental restorative resin composite material ceases after a short period of time. Fherefore, the longterm therapeutic effectiveness of fluoride-containing dental resin composite is questionable. Dental etchants and tooth surface conditioners, such as oral rinses, containing anti-microbial agents have also been disclosed. U.S. Pat. No. 4,939,132 to Colburn et al. discloses 5-alkylsulfonylsalicylanilides and their use as antiseptic compositions having anti-microbial activity against organisms such as *Streplococcus mutans*. However, these materials also provide only a temporary anti-microbial effect as they are rinsed off or otherwise removed from the tooth.

One approach to resolving this problem is disclosed in U.S. Pat. No. 5,408,022 and 5,733,949 to Imazato et al., which disclose anti-microbial polymerizable compositions comprising an ethylenically unsaturated monomer, at least one mono-, di-, or tri-functional ethylenically unsaturated monomer having anti-microbial activity, and a polymerization initiator. While suitable for their intended purposes, these compositions are restricted to use of copolymerizable anti-bacterial agents which are expensive and/or of limited availability.

Accordingly, there remains a need in the art for anti-microbial dental compositions suitable for use as dental primers and adhesives, liners, sealants, luting cements, and restorative materials that will sustain anti-microbial activity after curing. There further remains a need for such anti-microbial dental compositions that will sustain anti-microbial activity over a period of time while not causing harm to the living dentin and surrounding tissues. There further remains a need for anti-microbial dental compositions, wherein the anti-microbial agent provided in the composition will not adversely affect the functioning of the composition's restorative properties.

SUMMARY OF THE INVENTION

The above-described and other drawbacks and deficiencies of the prior art are overcome or alleviated by the anti-microbial dental restorative composition of the present invention. comprising a polymerizable component, a polymerization initiator system, and an anti-microbial agent selected from the group consisting of salicyclic acid, salicyclic acid esters, sulfanilamide or combinations thereof. Preferably, the dental restorative composition is in the form of an adhesive or filling composition.

A preferred embodiment provides a method for restoring a tooth comprising preparing an area of a tooth to be restored, applying an anti-microbial bonding adhesive to the surface of the area to be restored, curing the anti-microbial bonding adhesive, filling the area with an anti-microbial dental filling composition, and curing the filling composition.

The above discussed and other features and advantages of the present invention will be appreciated and understood by those skilled in the art from the following detailed description.

DETAILED DESCRIPTION OF THE PREFERRED EMBODIMENTS

A permanent or long-acting antimicrobial dental restorative composition comprises a polymerizable component, a polymerization system, and an anti-microbial agent selected from the group consisting of salicylic acid, salicylic acid esters, sulfanilamide, or combinations thereof. These compositions are suitable for restoring the functionality and anatomy of a damaged tooth. Uses include, but are not limited to, use as dental primers, adhesives, surface sealants, liners, luting cements, and composite restoratives that will impart anti-microbial activity to the contacted tooth structure.

The present anti-microbial dental compositions comprise a polymerizable component, i.e., at least one polymerizable monomer or prepolymer selected from those known in the art of dental materials, including but not being limited to polymerizable amides, esters, olefins, imides, acrylates, methacrylates, urethanes, vinyl esters or epoxy-based materials. Other polymerizable components include those based on styrene, styrene acrylonitrile, sulfones, acetals, carbonates, phenylene ethers, phenylene sulfides, and the like.

Preferred polymerizable monomers are ethylenically unsaturated and include those based on acrylic and methacrylic monomers, for example those disclosed in U.S. Pat. No. 3,066,112, U.S. Pat. No. 3,179,623, and U.S. Pat. No. 3,194,784 to Bowen; U.S. Pat. No. 3,751,399 and U.S. Pat. No. 3,926,906 to Lee et al.; and commonly assigned U.S. Pat. No. 5,276,068 to Wakline, all of which are herein incorporated by reference in their entirety. Methacrylate-based monomers are particularly preferred, including the condensation product of bisphenol A and glycidyl methacrylate, 2,2'-bis [4-(3 -methacryloxy-2-hydroxy propoxy)-phenyl]-propane ("BIS-GMA"), dipentaerythritol pentaacrylate (DPEPA), pentaerythritol dimethacrylate (PEDM), the condensation product of ethoxylated bisphenol A and glycidyl methacrylate ("EBPA-DMA"), and the condensation product of 2 parts hydroxymethylmethacrylate and 1 part triethylene glycol bis(chloroformate) ("PCDMA"). Polyurethane-based dimethacrylates ("PUDMA") are also within the scope of the present invention.

The polymerizable component may further comprise additional polymerizable diluent monomers. Such monomers are generally used to adjust the viscosity of the polymerizable composition. Suitable methacrylate-based diluent monomers include, without limitation, hydroxyalkyl methacrylates, such as 2-hydroxyethyl methacrylate, 1,6-hexanediol dimethacrylate, and 2-hydroxypropyl methacrylate; glyceryl dimethacrylate; and ethyleneglycol methacrylates, including ethyleneglycol methacrylate, diethyleneglycol methacrylate, triethyleneglycol methacrylate and tetraethyleneglycol methacrylate. Triethyleneglycol dimethacrylate ("TEGDMA") is particularly preferred.

When used as primers, adhesives, or primer/adhesive restorative dental compositions, the polymerizable component preferably comprises a hydrophilic polymerizable monomers to enhance the bonding characteristics of the composition. Suitable polymerizable hydrophilic monomers may have carboxyl, phosphoryl, sulfonyl, and/or hydroxyl functional groups. Examples of polymerizable hydrophilic monomers having at least one carboxyl group include but are not limited to methacrylic acid, maleic acid p-vinylbenzoic acid, 11-methacryloyloxy-1,1-undecanedicarboxylic acid, 1,4-dimethacryloyloxyethylpyromellitic acid, 6-methacryloyloxyethylnaphthalene-1,2,6-tricarboxylic acid, 4-methacryloyloxymethyltrimellitic acid and the anhydride thereof, 4-methacryloyloxyethyltrimellitic acid ("4-MET") and an anhydride thereof ("4-META"), 4-(2-hydroxy-3-methacryloyloxy) butyltrimellitic acid and an anhydride thereof, 2,3-bis(3,4-dicarboxybenzoyloxy)propyl methacrylate, methacryloyloxytyrosine, N-methacryloyloxytyrosine, N-methacryloyloxyphenylalanine, methacryloyl-p-aminobenzoic acid, an adduct of 2-hydroxyethyl methacrylate with pyromellitic dianhydride (PMDM), and an adduct of 2-hydroxyethyl methacrylate with 3,3', 4,4'-benzophenonetetracarboxylic dianhydride (BTDA) or 3,3', 4,4'-biphenyltetracarboxylic dianhydride. Presently preferred hydrophilic monomers include BPDM, the reaction product of an aromatic dianhydride with an excess of 2-HEMA (2-hydroxyethyl methacrylate), as disclosed in U.S. Pat. No. 5,348,988, which is incorporated by reference herein. Other presently preferred hydrophilic monomers include EDMT, the reaction product of 2-hydroxyethyl methacrylate ("2-HEMA") with ethylene glycol bistrimellitate dianhydride; DSDM, the reaction product of 3,3',4,4'-diphenylsulfone tetracarboxylic dianhydride and 2-HEMA; PMDM, and PMGDM, the adduct r of pyromellitic dianhydride with glycerol dimethacrylate.

Examples of polymerizable monomers having at least one phosphoric acid group include 2-methacryloyloxyethyl acidophosphate, 2-methacryloyloxypropyl acidophosphate, 4-methacryloyloxybutyl acidophosphate, 8-methacryloyloxyoctyl acidophosphate, 10-methacryloyloxydecyl acidophosphate, bis(2-methacryloyloxyethyl)acidophosphate, 2 methacryloyloxyethylphenyl acidophosphate. The phosphoric acid group in these compounds may be replaced with a thiophosphoric acid group. Preferred are 2-methacryloyloxyethylphenyl acidophosphate and 10-methacryloyloxydecyl acidophosphate. Examples of polymerizable monomers having at least one sulfonic acid group include 2-sulfoethyl methacrylate, 3-sulfo-2-butyl methacrylate, 3 -bromo-2-sulfo-2-propyl methacrylate, 3 -methoxy-1-sulfo-2-propyl methacrylate, and 1,1-dimethyl-2-sulfoethyl methacrylamide. Preferred is 1,1-dimethyl-2-sulfoethyl methacrylamide.

All the above polymerizable monomers may be used alone or in combination.

The dental restorative composition furthermore includes a polymerization initiator system, including light curing, self-curing, dual curing, and vacuum, heat, and pressure curing systems as well as any combination thereof. Visible light curing systems employ light-sensitive compounds such as benzil diketones, and in particular, DL-camphorquinone in amounts ranging from about 0.05 to 0.5 weight percent. Visible light curing systems furthermore preferably comprise polymerization accelerators, which include various organic tertiary amines well known in the art. In visible light curable compositions, the tertiary amines are generally acrylate derivatives such as dimethylaminoethyl methacrylate and, particularly, diethylaminoethyl methacrylate ("DEAME") in amounts in the range from about 0.05 to 0.5 weight percent.

Self-curing compositions will generally contain free radical polymerization initiators such as, for example, a peroxide in amounts ranging from about 2 to 6 weight percent. Particularly suitable free radical initiators are lauryl peroxide, tributyl hydroperoxide, cumene hydroperoxide, and, more particularly benzoyl peroxide. The heat and pressure curable systems also include a heat cure initiator such as aromatic sulfinic acids and salts thereof, benzoyl peroxide, 1,1'-azobis (cyclohexanecarbonitrile), or other free radical initiators. Polymerization accelerators commonly used with these include tertiary amines, generally aromatic tertiary amines such as ethyl 4-(N,N-dimethyl) aminobenzoate ("EDAB"), dimethyl-p-toluidine, dihydroxyethyl-p-toluidine and the like, in amounts ranging from about 0.05 to about 4.0 weight percent.

The dental restorative compositions may also comprise other additives and solvents known in the art, for example, ultra-violet light absorbers, anti-oxidants such as BHT, stabilizers, fillers, pigments, opacifiers, handling agents, and others. It is preferred to employ an ultraviolet absorber in amounts ranging from about 0.05 to about 5.0 weight percent. Such UV absorbers are particularly desirable in the visible light curable compositions in order to avoid discoloration of the resin from any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y.

Fillers, such as colloidal silica, barium glasses, fibrous fillers, quartz, ceramic fillers and the like may also be incorporated into the compositions, particularly when they are to be used as bonding agents, luting cements or filling composites. Suitable fillers include fillers conventionally used in the dental industry capable of being covalently bonded to the resin matrix itself or to a coupling agent which is covalently bonded to both. Silane coupling agents are known, for example methacryloxypropyl trimethoxy silane. Such fillers are described in U.S. Pat. Nos. 4,544,359 and 4,547,531, the pertinent portions of which are hereby incorporated by reference. Examples of suitable filling materials include but are not limited to amorphous silica, spherical silica, colloidal silica, barium glasses, quartz, ceramic fillers, silicate glass, hydroxyapatite, calcium carbonate, fluoroaluminosilicate, barium sulfate, quartz, barium silicate, strontium silicate, barium borosilicate, barium boroaluminosilicate, strontium borosilicate, strontium boroaluminosilicate, glass fibers, lithium silicate, ammoniated calcium phosphate, deammoniated calcium phosphate, alumina, zirconia, tin oxide, polymer powders, polymethyl methacrylate, polystyrene, and polyvinyl chloride, titania, and combinations thereof. Particularly suitable fillers for dental filling-type materials prepared are those having a particle size in the range from about 0.1 to about 5.0 microns, together with a silicate colloid having particle sizes in the range from about 0.001 to about 0.07 microns.

A variety of dentally acceptable antimicrobial agents are known, including chlorhexidine and erythromycin, among others. Agents suitable for use in the present compositions, which are to be used as dental primers, adhesives, primer/adhesives, bonding agents, liners, luting cements, and fillers, must be generally effective against the organisms which cause secondary decay, and must not adversely affect the required physical properties of the cured compositions, in particular water sorption, diametral tensile strength, and hardness. In particular, the ADA specification No. 27 requires dental resin composites to have water sorption values below 50 $\mu g/mm^3$/week. Commercial dental restorative materials used as, filling materials preferably have water sorption values of less than about 30, more preferably less than about 20, and most preferably less than about 15 $\mu g/mm^3$/week. The ADA specification No. 27 also specifies that the diametral tensile strength for filled dental composite (type II) should be a minimum of 34 MPa. Commercial dental restorative materials used as filling materials preferably have DTS values of greater than about 38, more preferably greater than about 40, and most preferably greater than about 45 MPa. Dentine bonding strength must be at least about 10 MPa, preferably at least about 15 MPa, more preferably at least about 18 MPA, and most preferably at least about 20 MPa. The inventors hereof have found that anti-microbial agent is selected from the group consisting of salicylic acid, 4-amino salicylic acid, esters of salicylic acid, esters of 4-aminosalicylic acid, and sulfanilamide fulfill these requirements. Combinations of the foregoing may also be used. The amino derivatives may be used in the form of a salt thereof, e.g., acetate, hydrochloride, or gluconate. Acceptable ester groups are branched or straight chain alkyl groups, preferably having from 1 to out 12 carbon atoms, or aromatic groups, preferably having from 6 to about 12 carbons atoms.

Without being bound by theory, the anti-microbial effect is understood to be primarily through the mode of competitive inhibition whereby the bacterial enzyme is inhibited due to the binding of the anti-microbial agent to the enzyme's active site. For example, para-aminobenzoic acid ("PABA") is an essential metabolite used by many bacteria to form nucleic acids. The anti-microbial agents p-aminosalicylic acid, and derivatives thereof, such as 4-phenyl aminosalicylate are chemically very similar to PABA. When these agents bind to the enzyme in place of PABA, the bacterium cannot make the folic acid necessary for synthesis of nucleic acid and other metabolic products. These enzymes are not present in animal cells, and therefore the anti-microbial agents do not disturb the metabolic activity of animal cells.

The compositions are desirably used as bonding primers or adhesives, and in particular as a one-bottle dentine primer/adhesive which forms a true barrier preventing growth of microorganisms on the tooth. When the compositions are to be used as bonding primers, adhesives, or primer/adhesives, volatile solvents such as water, alcohol, acetone, and the like are used to dilute the polymerizable monomer(s), and the compositions preferably comprise an antimicrobial agent in an amount of about 0.1 weight percent (wt. %) to about 5.0 wt. %, more preferably from about 0.5 wt. % to about 3.0 wt. %; polymerizable, preferably hydrophilic, monomer/prepolymer in an amount of about 1 wt. % to about 70 wt %, more preferably from about 20 wt. % to about 50 wt. %; a polymerization inititiator in an amount from about 0.05 to about 5 wt. %; and solvent in an amount of about 0 wt. % to about 90 wt. %, more preferably about 20 wt. % to about 90 wt. %, most preferably about 30 wt. % to about 70 wt. % (based on the total weight of the composition). The particular amounts of polymerizable monomer(s) and solvent are adjusted so as to provide sufficient viscosity such that they can be applied in one or a relatively few number of coats and achieve a uniform thin coating, of the dental substrate, while providing high bonding strengths between the dental substrate and the restorative material or dental component. Optionally, additional polymerizable monomers, optional self-life stabilizers, or other modifying ingredients known in the art can also be incorporated.

The compositions can also be used as a bonding agent and/or base liner under restorative materials such as resin composites, silver amalgam alloys, and the like. When used underneath such restorative materials, it is preferable to have an antimicrobial agent present in an amount of about 0.1 to about 5.0 wt. %, more preferably about 0.5 to about 3.0 wt. %: a polymerizable monomer in an amount of about 10 to about 80 wt. %, more preferably about 30 to about 70 wt. %; a polymerization inititiator in an amount from about 0.05 to about 5 wt. %; and at preferably a diluent polymerizable monomer in an amount of about 20 to about 90 wt. %, more preferably about 30 to about 70 wt. % (based on the total weight of the composition). Modifying agents such as fillers, e.g., up to about 10 wt. %, pigments, opacifiers, antioxidants/shelf-life stabilizers known in the art may also be included.

When used as dental luting cements and/or cavity filling materials, the compositions comprise an antimicrobial agent present in an amount of about 0.1 to about 5.0 wt. %, more preferably about 0.5 to about 3.0 wt. %; a polymerizable monomer in an amount of about 5 to about 60 wt. %, more preferably about 10 to about 40 wt. %; a diluent polymerizable monomer in an amount of about 5 to about 60 wt. %, more preferably about 10 to about 40 wt. %; a polymerization inititiator in an amount from about 0.05 to about 5 wt. %; and filler, preferably in an amount of about 40 to about 90 wt. % based upon the total weight of the composition.

A preferred embodiment provides a method for restoring a tooth comprising preparing an area of a tooth to be restored, applying an anti-microbial primer/adhesive, and curing the anti-microbial bonding adhesive. The restoration is then filled, optionally with an anti-microbial dental filling composition, and the filling composition is cured.

The invention is further illustrated by the following non-limiting examples.

EXAMPLES

All parts are parts by weight based on the total composition unless indicated otherwise.

Examples 1–16 have been prepared as set forth in Tables 1A and 1B. Examples 1, 6 and 13 are controls, having no added antimicrobial agent.

TABLE 1A

| COMPONENT | EXAMPLE NO. | | | | | | | |
|---|---|---|---|---|---|---|---|---|
| | 1* | 2 | 3 | 4 | 5 | 6* | 7 | 8 |
| Bis-GMA | 60 | 60 | 60 | 60 | 60 | 3 | 3 | 3 |
| PCDMA | — | — | — | — | — | — | — | — |
| 2-HEMA | 40 | 40 | 40 | 40 | 40 | 20 | 20 | 20 |
| PMGDM | — | — | — | — | — | 15 | 15 | 15 |
| TEGDMA | — | — | — | — | — | — | — | — |
| EBPA-GMA | — | — | — | — | — | — | — | — |
| Camphorquinone | 0.17 | 0.17 | 0.17 | 0.17 | 0.17 | 0.2 | 0.2 | 0.2 |
| DEAMA | 0.23 | 0.23 | 0.23 | 0.23 | 0.23 | 0.2 | 0.2 | 0.2 |
| BHT | — | — | — | — | — | 0.01 | 0.01 | 0.01 |
| UV-5411 | — | — | — | — | — | — | — | — |
| EDAB | — | — | — | — | — | — | — | — |
| 4-Aminosalicylic acid | — | 0.5 | 3 | — | — | — | 0.5 | — |
| Phenyl-4-aminosalicylate | — | — | — | — | — | — | — | — |
| Sulfanilamide | — | — | — | 0.5 | 3 | — | — | 0.5 |
| Barium borosilicate | — | — | — | — | — | — | — | — |
| Fumed silica | — | — | — | — | — | — | — | — |
| Acetone | — | — | — | — | — | 55 | 55 | 55 |
| Distilled water | — | — | — | — | — | 6 | 6 | 6 |
| Spherical Silica | — | — | — | — | — | — | — | — |
| Silane | — | — | — | — | — | — | — | — |

*Control

TABLE 1B

| COMPONENT | EXAMPLE NO. | | | | | | | |
|---|---|---|---|---|---|---|---|---|
| | 9 | 10 | 11 | 12 | 13* | 14* | 15 | 16 |
| Bis-GMA | 60 | 60 | 4 | 4 | 4 | — | — | — |
| PCDMA | — | — | — | — | — | 7 | 7 | 7 |
| 2-HEMA | 40 | 40 | — | — | — | — | — | — |
| PMGDM | — | — | — | — | — | — | — | — |
| TEGDMA | — | — | 13 | 13 | 13 | — | — | — |
| EPA-GMA | — | — | 13 | 13 | 13 | 16 | 16 | 16 |
| Camphorquinone | 0.17 | 0.17 | 0.10 | 0.10 | 0.10 | 0.06 | 0.06 | 0.06 |
| DEAMA | 0.23 | 0.23 | — | — | — | 0.09 | 0.09 | 0.09 |
| BHT | — | — | 0.01 | 0.01 | 0.01 | — | — | — |
| UV-5411 | — | — | 0.24 | 0.24 | 0.24 | 0.17 | 0.17 | 0.17 |
| EDAB | — | — | 0.10 | 0.10 | 0.10 | — | — | — |
| 4-Aminosalicylic acid | — | — | 3 | — | — | — | — | — |
| Phenyl-4-aminosalicylate | 0.5 | 3 | — | — | — | — | 0.69 | 0.69 |
| Sulfanilamide | — | — | — | 3 | — | — | — | — |
| Barium borosilicate | — | — | 60 | 60 | 60 | 68 | 68 | 68 |
| Fumed silica | — | — | 1 | 1 | 1 | 7.7 | 7.7 | 7.7 |
| Spherical silica | — | — | 8.5 | 8.5 | 8.5 | — | — | — |
| Silane | — | — | 1.36 | 1.36 | 1.36 | 1.3 | 1.3 | 1.3 |
| Acetone | — | — | — | — | 55 | 55 | — | — |
| Distilled water | — | — | — | — | 6 | 6 | — | — |

*Control

Water sorption was evaluated in accordance with ADA specification No. 27 which is incorporated by reference herein. Three samples of specimen discs (15±1 mm in diameter and 0.5±0.1 mm thickness) from each sample were prepared and placed in sample molds. Each sample was packed into the mold, covered with a glass slide, and cured for about 40 seconds using an Optilux 400 visible light cure unit (available from Demetron Research Corporation, CT). The prepared samples were then treated according to ADA specification No. 27 and water sorption (Wsp) results were calculated according to the following formula.

$$Wsp = \frac{M_2 - M_1}{V}$$

wherein:

$M_2$ is the mass of the specimen, in micrograms, after immersion in water 7 days;

$M_1$ is the original mass of the specimen, in micrograms; and

V is the volume of the specimen in cubic millimeters.

Diametral tensile strength (DTS) tests were performed in accordance with ADA specification No. 27, which is incorporated by reference herein. Samples were placed in a splitable stainless steel mold (3 mm high and 6 mm inside diameter) resting on a glass slide. Another glass slide was applied on the top after filling the composite material into the mold and the material visible light cured for 40 seconds on top and bottom with an Optilux 400 unit (available from Demetron Research Corporation, CT). The sample was then removed from the mold and aged for about 24 hours at 37° C. in water. The samples were then tested on an Instron and DTS was computed as follows:

$$DTS = \frac{2P}{\pi dl}$$

where in:

DTS=diametral tensile strength in MPa;

P=load at fracture (N);

d=diameter of specimen (mm);

$\pi$=3.14 l=length of the specimen (mm)

Water sorption, solubility, and flexural strength of Comparative Example 14 and Examples 15 and 16 were evaluated as described above. Cytotoxicity and antimicrobial effect were tested by Loma Linda University. (Biocompatibility and Toxicology Research Laboratory) according to the standard Agar diffusion test method. The evaluation of cytotoxicity test for the materials were following the procedures specified in ISO 10993-5 (1992) and ISO 7405 (1997). Tables 2 and 3 provide test results for comparative Example 14, and Examples 15 and 16.

TABLE 2

| Example | Water Sorption (S.D.), µg/mm³/week | Solubility in Water (S.D.), µg/mm³week | Flexural Strength (S.D.), psi |
|---|---|---|---|
| 14* | 8.7 (0.46) | 4.1 (2.2) | 13688 (1804.8) |
| 15 | 9.6 (0.26) | 3.6 (0.36) | 12708 (2399.0) |
| 16 | 10.8 (0.56) | 2.9 (1.51) | 14942 (2845.1) |

*Control

TABLE 3

Cytotoxicity and Antimicrobial Effects

| Example | Cytotoxicity based on Agar Diffusion | Cytotoxicity of the Material Extracts | Inhibition Zone (mm) on S. mutans |
|---|---|---|---|
| 14* | None | None | — |
| 15 | None | None | 9.67 ± 0.76 |
| 16 | None | None | 9.63 ± 0.18 |

*Control

From the results, it can be seen that the addition of the anti-microbial agent, in particular salicylic acid and its derivatives, into the present dental resin system does not adversely effect the physical and mechanical properties of the material. Further, it can be seen that the addition of anti-microbial agent does not affect the cytotoxicity of the composition, while simultaneously providing the desired anti-microbial effect.

Anti-microbial activity of Comparative Example 1, Example 2 and Example 5 were evaluated for oral cariogenic bacterial strains of *Strepltococcus mutans* (ATCC 25175), and *Actinomyces viscosus* (ATCC 43146), obtained from the American Type Culture Collection, Rockville, Md. The examples were evaluated both unpolymerized and after polymerization. Sterile physiological saline (0.9%) was used as the negative control, and Peridex (chlorhexidine, available from Proctor and Gamble, Cincinnati, Ohio) served as the positive control. Accordingly, samples of the polymerized Comparative Example 1 and Examples 2 and 5 were prepared and delivered into a clean Teflon ring (6 mm in inner diameter and 1 mm in height) and placed on a glass slide. The examples were then light cured for 20 seconds (Optilux, Demetron Research Corporation, CT) under a matrix (Mylar) strip. Fresh overnight cultures were prepared for each microbial strain by inoculating 1.5 mL frozen stock into 25 mL of Mueller Hinton Broth (MHB, 21 g/L). The cultures were incubated at 37° C. with 5% $CO_2$ for approximately 16 hours. Purity of cultures was examined by Gram stain and by plating on standard bacteriological media (MHB with 1.5% Bacto agar) for colony observation. The cultures were inoculated on MHB agar plates (1.5% Bacto agar) by streaking the entire surface of the plate using, a sterile cotton tipped applicator. Plates were allowed to dry for approximately 5 minutes, but no longer than 15 minutes before the placement of the samples. For uncured examples, 10 µL, of the test material was delivered to a sterile filter disk (6 mm in diameter), which was then placed on the inoculated agar. For cured examples, the prepared specimens were placed directly on the inoculated agar. The plates were then inverted and incubated at 37° C. in 5% $CO_2$. Each plate was observed and measured for the diameter of the zone of inhibition (in millimeters) at 24, 48 and 72 hours. Means and standard deviations of inhibition zones calculated for each group. The homogeneity of variances was examined using Box's method. One-way analysis of variance (ANOVA) was used when the variances were determined to be homogeneous; otherwise the Welch test replaced the ANOVA. The Newman-Keul's method was used to examine differences in means amono groups. Results are shown in Tables 4 and 5.

TABLE 4

Anti-microbial Activity in *S. mutans* (ATCC 25175)

| | Zone of Inhibition (mm in diameter) | | |
|---|---|---|---|
| Sample | 24 hours | 48 hours | 72 hours |
| Negative (Saline) | 0.0 ± 0.0[a] | 0.0 ± 0.0 | 0.0 ± 0.0 |
| 1* (Cured) | 5.0 ± 1.0 | 5.0 ± 1.0 | 4.7 ± 1.5 |
| 2 (Cured) | 9.3 ± 0.6 | 10.7 ± 1.2 | 10.3 ± 0.6 |
| 5 (Cured) | 10.7 ± 1.5 | 13.0 ± 3.6 | 12.7 ± 3.1 |
| 1* (Uncured) | 12.3 ± 0.6 | 14.6 ± 2.9 | 14.9 ± 2.1 |
| 2 (Uncured) | 14.5 ± 1.5 | 15.3 ± 3.2 | 15.0 ± 3.5 |
| 5 (Uncured) | 18.3 ± 2.1 | 19.7 ± 0.6 | 19.3 ± 3.2 |
| Positive (Peridex) | 18.7 ± 1.5 | 21.7 ± 3.8 | 19.3 ± 0.6 |

*Control

The anti-microbial activity of Comparative Example, and Examples 2 and 3 against *S. mutans* are shown in Table 4. The variances were determined to be homogeneous. Both uncured and cured adhesives examples showed anti-microbial activities, as evidenced by the presence of the inhibition zones. The uncured materials had greater anti-microbial activity than the cured materials. The addition of 0.5 parts 4-aminosalicylic acid or 3 parts sulfanilamide appeared to increase the anti-microbial activity of the adhesives. However, little increase was observed in the average diameter of the inhibition zone over time.

TABLE 5

Anti-microbial Activity in *A. viscous* (ATC 43146)

| | Zone of Inhibition (mm in diameter) | | |
|---|---|---|---|
| Materials | 24 hours | 48 hours | 72 hours |
| Negative (Saline) | 0.0 ± 0.0[a] | 0.0 ± 0.0 | 0.0 ± 0.0 |
| 1* (Cured) | 4.3 ± 1.5 | 4.3 ± 1.4 | 4.0 ± 1.7 |
| 2 (Cured) | 8.0 ± 0.1 | 8.0 ± 0.2 | 7.6 ± 0.6 |
| 5 (Cured) | 9.7 ± 1.5 | 10.3 ± 5.1 | 9.3 ± 1.2 |
| Positive (Peridex) | 12.0 ± 0.2 | 14.3 ± 0.6[b] | 12.0 ± 0.6 |
| 1* (Uncured) | 11.0 ± 0.2 | 11.3 ± 0.6[b] | 10.7 ± 0.6 |
| 2 (Uncured) | 14.0 ± 5.2 | 17.3 ± 5.9 | 16 ± 4.4 |
| 5 (Uncured) | 18.8 ± 9.7 | 20.7 ± 7.2 | 19.3 ± 3.2 |

*Control

The results observed for *A. viscosus* are summarized in Table 5. The data were found to lack homogeneity in variances, and therefore, the Welch test was used for the data analysis. Anti-microbial activity was again detected in both the uncured and cured adhesives and the uncured materials induced greater inhibition zones than the cured materials. However, the numerically higher values of inhibition zones induced by the uncured adhesives with 0.5 parts para-aminosalicylic acid or 3 parts sulfanilamide were not significantly different ($p > 0.05$) from those of the positive control. This is believed to be due to the large standard deviations and the lack of the homogeneity in variances of the data.

Dentine bonding strength was evaluated using the present compositions as formulated for use as a one bottle dentine primer/adhesive. A series of thirty recently extracted human molars, free of caries and obvious mechanical defects, were selected for adhesion of three dentine bonding agents control primer/adhesive (Comparative Example 6); primer/adhesive with p-amino-salicylic acid (Example 7); and primer/adhesive with sulfanilamide (Example 8). In each case, the teeth were stored in 0.05% thymal solution and transferred to deionized room temperature water for at least 24 hours. Prior to preparation, the teeth were mounted in a special ring holder (BenCore testing device, available from Denville Engineering, California) by means of a self-cure acrylic resin. The occlusal aspect of the tooth was removed by means of a rotating diamond blade. The sectioned plane was essentially perpendicular to the long axis of the tooth. Care was taken to restrict the sectioned surface to dentin only. The sectioned region of the occlusal dentin was surfaced down to a 600 grit using conventional metallographic procedures. Surfacing was carried out by means of silicon carbide papers in the presence of water.

The surfaces to be bonded were washed thoroughly to remove debris, dried, and the teeth samples were divided into two groups: Group 1 was subjected to acid etch prior to applying the primer/adhesive; Group 2 was placed directly in contact with the bonding agents as described below. Each group was then divided into three subgroups to receive the three primer/adhesives (five samples per subgroup).

Each of the specimens of Group 1 were generated by with etching by:
  (1) Applying a 37% concentration of $H_3PO_4$ to the dentinal surface for about 20 seconds;
  (2) Washing with tap water for about 15 seconds;
  (3) Air drying for 2 seconds;
  (4) Applying two coats of the adhesive with a brush;
  (5) Air dispersing and evaporating the solvents(s);
  (6) Light curing for 10 seconds (using an Optilux 400, available from Demetron, CT); and
  (7) Filling the ring with (Conquest Crystal A2, available from Jeneric/Pentron, CT) in two increments and light curing 40 seconds, each.

Each of the specimens of Group 2 were generated without etching by steps 4–7 above.

Upon completion of the bonding procedure, the BenCore ring fixture was removed from the specimen surface and the specimens were stored for 24 hours in water at 37° C. The specimens were positioned on the BenCore Multi-T Testing Apparatus and set in a shear testing mode on an Instron Testing Machine. With the specimen in a horizontal position, care was taken so that the guillotine blade was able to move freely up and down and passively engage the stub on the bonded surface. A vertical force was applied with a cross head speed of 0.5 mm per minute until the specimen is debonded. The result was recorded and summarized below. Dentin Bond Strength (DBS) was calculated as follows:

$$DBS = \frac{P}{A^2}$$

wherein:
  P is the load at which the adhesion is debonded; and
  $A^2$ is the bonding surface area of the composite on dentin.
Results are shown in Table 6.

TABLE 6

Results of Dentin Bonding Strength

| Example | DBS (S.D.), MPa Dentine Etched | DBS MPa (S.D.) No Dentine Etch |
|---|---|---|
| 6* | 22.5 (2.5) | 18.3 (2.1) |
| 7 | 24.1 (1.6) | 18.3 (1.2) |
| 8 | 22.2 (2.3) | 18.7 (1.0) |

Table 6 shows the advantageous dentin bonding achieved with the present one bottle primer/adhesives. Further, the addition of 0.5 wt. % anti-microbial agent p-aminosalicylic acid or sulfanilamide into the resin primer/adhesive did not interfere with the bonding strength to the dentin. In fact, in Example 7, a slight improvement on the dentin bond strength was observed.

Use of the present compositions as bonding agents, surface sealants, and/or base liners when restoring a tooth in conjunction with other restorative dental materials, was demonstrated as follows. Formulations according to Comparative Example 1 and Examples 2–5 and 9–10 as set forth in Table 1 were prepared to be used as bonding agent, surface sealant, and/or base liner when restoring a tooth in conjunction with other restorative dental materials. For unfilled resin formulations, testing of the surface hardness upon the polymerization of the resin is a common method to define the curing and mechanical property of a resin material. Barcol Hardness (BH) testing was performed on the exemplary formulation using a Barcol Hardness Tester GYZJ 935 (available from Barber Colman Co., Illinois) after the compositions were subject to 40 seconds of light curing with an Optilux 400 visible light curing unit at one millimeter thickness in a stainless steel mold of 1×10 mm dimension. Three samples for each composition were tested and five BH readings were performed on the top surface (surface receiving light cure) and the bottom and recorded for each sample. The testing results are summarized in Table 7.

TABLE 7

| | Barcol Hardness | |
|---|---|---|
| Examples | BH at Top (S.D.) | BH at Bottom (S.D.) |
| 1* | 70 (3.0) | 65 (2.8) |
| 2 | 63 (2.5) | 60 (2.5) |
| 3 | 55 (3.0) | 50 (2.8) |
| 4 | 72 (2.7) | 65 (3.0) |
| 5 | 70 (3.0) | 65 (3.0) |
| 9 | 78 (2.5) | 73 (2.2) |
| 10 | 80 (2.8) | 75 (2.5) |

*Control

Comparison of the control (Example 1) without the addition of an anti-microbial agent to Examples 9 and 10 show that the addition of phenyl aminosalicylic acid at 0.5 wt. % (Example 9) and 3.0 wt. % (Example 10) does not interfere with the hardness of the resin upon polymerization, and actually improves the material hardness. The acid form of the aminosalicylic acid, (Examples 2 and 3) however, does somewhat lower the hardness of the resin composition.

The influence of the addition of 3 wt. % anti-microbial agent were evaluated for water sorption and diametral tensile strength (DTS) for Examples 11 and 12 according to ADA specification No. 27. Comparative Example 13 served as a control.

TABLE 8

| | Water Sorption and Diametral Tensile Strength | |
|---|---|---|
| Example | WS (S.D.), $\mu g/mm^3$ | DTS (S.D.), MPa |
| 13* | 11.52 (0.35) | 48.7 (7.9) |
| 11 | 11.88 (0.23) | 51.2 (6.8) |
| 12 | 12.32 (0.40) | 35.8 (7.2) |

*Control

The results in Table 8 demonstrate that the addition of an anti-microbial agent into filled composite resins in the amount of about 3 wt. % showed comparable results in water sorption to the control. The addition of the phenyl aminosalicyla.te showed a slight increase in DTS compared to the control. The addition of sulfanilamide, however, did not show such an increase. Phenyl aminosalicylate is preferred in the formulation.

A two-part self curable resin composition was prepared for use as a self-curable bonding agent or a base liner comprised of a Part A and a Part B. The formulation of Part A was similar to Example 2 with the addition of 0.5 parts of the phenyl ester of aminosalicylic acid, and with the light curing initiation ingredients replaced by about 1 wt. % of a tertiary amine reducing agent, N,N-dimethyl-p-toluidine. The formulation of Part B is similar to Part A, except about 1.5 percent of benzoyl peroxide replaces the amine. Upon mixing a 1:1 ratio of the two parts, the material gives a working time of about 2 minutes and hardens completely in about 3 minutes. The two-part resin formulation can be used as a self-curable bonding agent or a base liner. When fillers are incorporated into the composition, the resin composite can also be used as self-curable luting cement and/or cavity filling material.

While the preferred embodiments of the invention have been set forth hereinabove it will be understood that modifications thereto are within the scope of the invention as the specific examples are provided by way of illustration and not limitation.

What is claimed is:

1. A dental restorative bonding primer, adhesive, base liner, primer/adhesive, luting cement or cavity filling material composition, comprising:
   a polymerizable component;
   a polymerization initiator system; and
   an anti-microbial agent selected from the group consisting of salicylic acid, 4-amino salicylic acid, esters of salicylic acid, esters of 4-aminosalicylic acid, and sulfanilamide, in an amount of about 0.1 wt. % to about 5 wt. % based on the total weight of the composition, wherein the water sorption of the cured dental restorative composition is less than about 50 $\mu g/mm^3$/week.

2. The dental restorative composition of claim 1, wherein the polymerizable component is selected from the group consisting of polymerizable amides, esters, olefins, acrylates, methacrylates, urethanes, vinyl esters, epoxy-based materials, styrene, styrene acrylonitrilc, sulfones, acetals, carbonates, phenylene ethers, phenylene sulfides, and combinations thereof.

3. The dental restorative composition of claim 1, wherein the polymerizable component comprises at least one monomer or prepolymer selected from the group consisting of 2,2'-bis [4-(3-methacryloxy-2-hydroxy propoxy)-phenyl]-propane, dipentaerythritol pentaacrylate, pentaerythritol dimethacrylate, the condensation product of ethoxylated bisphenol A and glycidyl methacrylate, the condensation product of 2 parts hydroxymethylmethacrylate and 1 part triethylene glycol bis(chloroformate), and polyurethane dimethacrylates.

4. The deurtal restorative composition of claim 3, wherein the polymerizable component further comprises a monomer selected from the group consisting of hydroxyalkl methacrylates, 2-hydroxyethyl methacrylate, 1,6-hexanediol dimethacrylate, 2-hydroxypropyl methacrylate, glyceryl dimethacrylate, ethyleneglycolmethacrylates, ethyleneglycol methacrylate, diethyleneglycol methacrylate, triethyleneglycol methacrylate.

5. The dental restorative composition of claim 3, wherein the polymerizable component further comprises a monomer selected from the group consisting of methacrylic acid, maleic acid p-vinylbenzoic acid, 11-methacryloyloxy-1,1- undecanedicarboxylic acid, 1,4-dimethacryloyloxyethylpyromellitic acid, 6methacryloyloxyethylnaphthalene-1,2,6-tricarboxylic acid, 4-methacryloyloxymethyltrimellitic acid and the anhydride thereof, 4-methacryloyloxyethyltrimellitic acid and an anhydride thereof, 4-(2-hydroxy-3-methacryloyloxy)bultytrimellitic acid and an anhydride thereof, 2,3-bis(3,4-dicarboxybenzoyloxy)propyl methacrylate, methacryloyloxytyrosine, N-methacryloyloxytyrosine, N-methacryloyloxyphenylalanine, methacryloyl-p-aminobenzoic acid, the adduct of 2-hydroxyethyl methacrylate with pyromellitic dianhydride, the adduct of 2-hydroxyethyl methacrylate with maleic anhydride, the adduct of 2-hydroxyethyl methacrylate with 3,3',4,4'-benzophenonetetracarboxylic dianhydride, the adduct of 2-hydroxyethyl methacrylale with 3,3',4,4'-biphenyltetracarboxylic dianhydride, the adduct of an aromatic dianhydride with an excess of 2-HEMA, the adduct of 2-HEMA with ethylene glycol bistrimellitate dianhydride, the adduct of 3,3',4,4'-diphenylsulfone tetracarboxylic dianhydide and 2-HEMA, the adduct of pyromellitic dianhydride with glycerol dimethacrylate, 2-methacryloyloxyethyl acidophosphate, 2-methacryloyloxypropyl acidophosphate, 4-methacryloyloxybutyl acidophosphate, 8-methacryloyloxyoctyl acidophosphate, 10-methacryloyloxydecyl acidophosphate, bis(2-methacryloyloxyethyl)acidophosphate, 2-methacryloyloxyethylphenyl acidophosphate, 2-sulfoethyl methacrylate, 3-sulfo-2-butyl methaclylate, 3-bromro-2-sulfo-2-propyl methacrylate, 3-methoxy-1-sulfo-2-propyl mathacrylate, and 1,1-dimethyl-2-sulfoethyl methacrylamide.

6. The dental restorative composition of claim 1, wherein the polymerization initiator system comprises an initiator selected from the group consisting of benzil diketones, DL-camphorquinone, peroxides, lauryl peroxide, tributyl hydroperoxide, cumene hydroperoxide, 1,1'-azobis (cyclohexanecarbonitrile), and benzoyl peroxide, and an accelerator selected from the group consisting of tertiary amines, dimethylaminoethyl methacrylate, diethylaminoethyl methacrylate, aromatic tertiary amines, 4-(N,N-dimethyl)aminobenzoate, dimethyl-p-toluidine, and dihydroxyethyl-p-toluidine.

7. The dental restorative composition of claim 1, wherein the anti-microbial agent is selected from the group consisting of 4-aminosalicylic acid, phenyl 4-aminosalicylate, salicylic acid, phenyl salicylate, and sulfanilamide.

8. The dental restorative composition of claim 1, further comprising one or more of ultra-violet light absorbers, anti-oxidants, stabilizers, fillers, pigments, opacifiers, or handling agents.

9. The dental restorative composition of claim 8, wherein the filler is selected from the group consisting of amorphous silica, spherical silica, colloidal silica, barium glasses, quartz, ceramic fillers, silicate glass, hydroxyapatite, calcium carbonate, fluoroaluminosilicate, barium sulfate, quartz, barium silicate, strontium silicate, barium borosilicate, barium boroaluminosilicate, strontium borosilicate, strontium boroaluminosilicate, glass fibers, lithium silicate, ammoniated calcium phosphate, deammoniated calcium phosphate, alumina, zirconia, tin oxide, polymer powders, polymethyl methacrylate, polystyrene, and polyvinyl chloride, titania, and combinations thereof.

10. The dental restorative composition of claim 1, further comprising a solvent.

11. The dental restorative composition of claim 1, wherein the anti-microbial agent is present in an amount of from about 0.5 to about 3.0 wt. %.

12. A dental bonding primer, adhesive, base liner, or primer/adhesive, comprising
   about 1 wt. % to about 90 wt. % of a polymerizable component;
   about 0.05 to about 5 wt. % of a polymerization initiator system;
   about 10 wt. % to about 90 wt. % of a solvent, and
   an anti-microbial agent selected from the group consisting of salicylic acid, 4-amino salicylic acid, esters of salicylic acid, esters of 4-aminosalicylic acid, and sulfanilamide, in an amount of about 0.1 wt. % to about 5 wt. %, based on the total weight of the composition, wherein the water sorption of the cured dental bonding primer, adhesive, base liner, or primer/adhesive is less than about 50 $\mu g/mm^3$/week.

13. The dental bonding primer, adhesive base liner, or primer/adhesive of claim 12, comprising
   about 30 wt. % to about 70 wt. % of a polymerizable component;
   about 0.05 to about 5 wt. % of a polymerization initiator system;
   about 20 wt. % to about 90 wt. % of a solvent, and
   an anti-microbial agent selected from the group consisting of salicylic acid, 4-amino salicylic acid, esters of salicylic acid, esters of 4-aminosalicylic acid, and sulfanilamide, in an amount of about 0.1 wt. % to about 5 wt. %, based on the total weight of the composition.

14. A dental luting cement or cavity filling material, comprising
   about 5 wt. % to about 60 wt. % of a polymerizable component;
   about 0.05 wt. % to about 5 wt. % of a polymerization initiator system;
   about 40 wt. % to about 90 wt. % of a filler; and
   an anti-microbial agent selected from the group consisting of salicylic acid, 4-amino salicylic acid, esters of salicylic acid, esters of 4-aminosalicylic acid, and sulfanilamide, in an amount of about 0.1 wt. % to about 5 wt. %, based on the total weight of the composition, wherein the water sorption of the cured luting cement or cavity filling material is less than about 50 $\mu g/mm^3$/week.

15. A dental luting cement or cavity filling material, comprising
   about 10 wt. % to about 40 wt. % of a polymerizable component;
   about 0.05 wt. % to about 5 wt. % of a polymerization initiator system;
   about 40 wt. % to about 90 wt. % of a filler; and
   an anti-microbial agent selected from the group consisting of salicylic acid, 4-amino salicylic acid, esters of salicylic acid, esters of 4-aminosalicylic acid, and sulfanilamide, in an amount of about 0.1 wt. % to about 5 wt. %, based on the total weight of the composition, wherein the water sorption of the cured luting cement or cavity filling material is less than about 50 $\mu g/mm^3$/week.

16. A dental restoration comprising the dental restorative composition of claim 1.

17. A dental restoration comprising the dental restorative composition of claim 12.

18. A dental restoration comprising the dental restorative composition of claim 14.

19. A dental restoration comprising the dental restorative composition of claim 15.

20. A method for restoring a tooth comprising:
preparing an area of a tooth to be restored;
applying the anti-microbial polymerizable adhesive dental composition of claim 12 to the area to be restored;
curing the anti-microbial bonding adhesive;
filling the area with a dental filling composition; and
curing the filling composition.

21. A bonding primer, adhesive, base liner, primer/adhesive, luting cement or cavity filling material composition comprising:
a polymerizable component comprising at least one monomer or prepolymer selected from the group consisting of 2,2'-bis [4-(3-methacryloxy-2-hydroxy propoxy)-phenyl]-propane, dipentaerythritol pentaacrylate, pentaerythritol dimethacrylate, the condensation product of ethoxylated bisphenol A and glycidyl methacrylate, the condensation product of 2 parts hydroxymethylmethacrylate and 1 part triethylene glycol bis(chloroformate), and polyurethane dimethacrylates;
a polymerization initiator system; and
an anti-microbial agent selected from the group consisting of salicylic acid, 4-amino salicylic acid, esters of salicylic acid, esters of 4-aminosalicylic acid, and sulfanilamide, in an amount of about 0.1 wt. % to about 5 wt. % based on the total weight of the composition, wherein the water sorption of the cured dental restorative composition is less than about 50 $\mu$g/mm$^3$/week.

22. The compositions of claim 21, wherein the anti-microbial agent is present in an amount of about 0.5 to about 3.0 wt. % based on the total weight of the composition.

23. The compositions of claim 21, wherein the polymerizable component further comprises a component selected from the group consisting of hydroxyalkyl methacrylates, 2-hydroxyethyl methacrylate, 1,6-hexanediol dimethacrylate, 2-hydroxypropyl methacrylate, glyceryl dimethacrylate, ethyleneglycolmethacrylates, ethyleneglycol methacrylate, diethyleneglycol methacrylate, triethyleneglycol methacrylate, tetraethyleneglycol methacrylate, methacrylic acid, maleic acid p-vinylbenzoic acid, 11-methacryloyloxy-1,1-undecanedicarboxylic acid, 1,4-dimethacryloyloxyethylpyromellitic acid, 6-methacryloyloxyethylnaphthalene-1,2,6-tricarboxylic acid, 4-methacryloyloxymethyltrimellitic acid and the anhydride thereof, 4-methacryloyloxyethyltrimellitic acid and an anhydride thereof, 4-(2-hydroxy-3-methacryloyloxy) butyltrimellitic acid and an anhydride thereof, 2,3-bis(3,4-dicarboxybenzoyloxy)propyl methacrylate, methacryloyloxytyrosine, N-methacryloyloxytyrosine, N-methacryloyloxyphenylalanine, methacryloyl-p-aminobenzoic acid, the adduct of 2-hydroxyethyl methacrylate with pyromellitic dianhydride, the adduct of 2-hydroxyethyl methacrylate with maleic anhydride, the adduct of 2-hydroxyethyl methacrylate with 3,3',4,4'-benzophenonetetracarboxylic dianhydride, the adduct of 2-hydroxyethyl methacrylate with 3,3',4,4'-biphenyltetracarboxylic dianhydride, the adduct of an aromatic dianhydride with an excess of 2-HEMA, the adduct of 2-HEMA with ethylene glycol bistrimellitate dianhydride, the adduct of 3,3',4,4'-diphenylsulfone tetracarboxylic dianhydride and 2-HEMA, the adduct of pyromellitic dianhydride with glycerol dimethacrylate, 2-methacryloyloxyethyl acidophosphate, 2-methacryloyloxypropyl acidophosphate, 4-methacryloyloxybutyl acidophosphate, 8-methacryloyloxyoctyl acidophosphate, 10-methacryloyloxydecyl acidophosphate, bis(2 methacryloyloxyethyl)acidophosphate, 2-methacryloyloxyethylphenyl acidophosphate, 2-sulfoethyl methacrylate, 3-sulfo-2-butyl methacrylate, 3-bromo-2-sulfo-2-propyl methacrylate, 3-methoxy-1-sulfo-2-propyl methacrylate, and 1,1-dimethyl-2-sulfoethyl methacrylamide.

24. The compositions of claim 21, wherein the polymerization initiator system comprises an initiator selected from the group consisting of benzil diketones, DL-camphorquinone, peroxides, lauryl peroxide, tributyl hydroperoxide, cumene hydroperoxide, 1,1'-azobis (cyclohexanecarbonitrile), and benzoyl peroxide, and an accelerator selected from the group consisting of tertiary amines, dimethylaminoethyl methacrylate, diethylaminoethyl methacrylate, aromatic tertiary amines, 4-(N,N-dimethyl)aminobenzoate, dimethyl-p-toluidine, and dihydroxyethyl-p-toluidine.

25. The compositions of claim 21, wherein the anti-microbial agent is selected from the group consisting of 4-aminosalicylic acid, phenyl 4-aminosalicylate, salicylic acid, phenyl salicylate, and sulfanilamide.

26. The compositions of claim 21, further comprising one or more of ultra-violet light absorbers, anti-oxidants, stabilizers, fillers, pigments, opacifiers, or handling agents.

27. The compositions of claim 26, wherein the filler is selected from the group consisting of amorphous silica, spherical silica, colloidal silica, barium glasses, quartz, ceramic fillers, silicate glass, hydroxyapatite, calcium carbonate, fluoroaluminosilicate, barium sulfate, quartz, barium silicate, strontium silicate, barium borosilicate, barium boroaluminosilicate, strontium borosilicate, strontium boroaluminosilicate, glass fibers, lithium silicate, ammoniated calcium phosphate, deammoniated calcium phosphate, alumina, zirconia, tin oxide, polymer powders, polymethyl methacrylate, polystyrene, and polyvinyl chloride, titania, and combinations thereof.

28. The compositions of claim 21, further comprising a solvent.

29. The compositions of claim 28, wherein the anti-microbial agent is present in an amount of from about 0.5 to about 3.0 wt. %.

30. A dental bonding primer, adhesive, base liner, or primer/adhesive composition, comprising
about 1 wt. % to about 90 wt. % of a polymerizable component comprising at least one monomer or prepolymer selected from the group consisting of 2,2'-bis [4-(3-methacryloxy-2-hydroxy propoxy)-phenyl]-propane, dipentaerythritol pentaacrylate, pentaerythritol dimethacrylate, the condensation product of ethoxylated bisphenol A and glycidyl methacrylate, the condensation product of 2 parts hydroxymethylmethacrylate and 1 part triethylene glycol bis(chloroformate), and polyurethane dimethacrylates;
about 0.05 to about 5 wt. % of a polymerization initiator system;
about 10 wt. % to about 90 wt. % of a solvent, and
an anti-microbial agent selected from the group consisting of salicylic acid, 4-amino salicylic acid, esters of salicylic acid, esters of 4-aminosalicylic acid, and sulfanilamide, in an amount of about 0.1 wt. % to about 5 wt. %, based on the total weight of the composition, wherein the water sorption of the cured dental bonding primer, adhesive, base liner, or primer/adhesive is less than about 50 $\mu$g/mm$^3$/week.

31. The compositions of claim 30, wherein the polymerizable component further comprises a component selected from the group consisting of hydroxyalkyl methacrylates, 2-hydroxyethyl methacrylate, 1,6-hexanediol dimethacrylate, 2-hydroxypropyl methacrylate, glyceryl dimethacrylate, ethyleneglycolmethacrylates, ethyleneglycol methacrylate, diethyleneglycol methacrylate, triethyleneglycol methacrylate, tetraethyleneglycol methacrylate, methacrylic acid, maleic acid p-vinylbenzoic acid, 11-methacryloyloxy-1,1-undecanedicarboxylic acid, 1,4-dimethacryloyloxyethylpyromellitic acid, 6-methacryloyloxyethylnaphthalene-1,2,6-tricarboxylic acid, 4-methacryloyloxymethyltrimellitic acid and the anhydride thereof, 4-methacryloyloxyethyltrimellitic acid and an anhydride thereof, 4-(2-hydroxy-3-methacryloyloxy) butyltrimellitic acid and an anhydride thereof, 2,3-bis(3,4-dicarboxybenzoyloxy)propyl methacrylate, methaeyloyloxytyrosine, N-methacryloyloxytyrosine, N-methacryloyloxyphenylalanine, methacryloyl-p-aminobenzoic acid, the adduct of 2-hydroxyethyl methaerylate with pyromellitie dianhydride, the adduct of 2-hydroxyethyl methacrylate with maleic anhydride, the adduct of 2-hydroxyethyl methacryl ate with 3,3',4,4'-benzophenonetetracarboxylic dianhydride, the adduct of 2-hydroxyethyl methacrylate with 3,3',4,4'-biphenyltetracarboxylic dianhydride, the adduct of an aromatic dianhydride with an excess of 2-HEMA, the adduct of 2-HEMA with ethylene glycol bistrimellitate dianhydride, the adduct of 3,3',4,4'-diphenylsulfone tetracarboxylic dianhydride and 2-HEMA, the adduct of pyromellitic dianhydride with glycerol dimethacrylate, 2-methacryloyloxyethyl acidophosphate, 2-methacryloyloxypropyl acidophosphate, 4-methacryloyloxybutyl acidophosphate, 8-methacryloyloxyoctyl acidophosphate, 10-methacryloyloxydecyl acidophosphate, bis(2-methacryloyloxyethyl)acidophosphate, 2-methacryloyloxyethylphenyl acidophosphate, 2-sulfoethyl methacrylate, 3-sulfo-2-butyl methacrylate, 3-bromo-2-sulfo-2-propyl methacrylate, 3-methoxy-1-sulfo-2-propyl methacrylate, and 1,1-dimethyl-2-sulfoethyl methacrylamide.

32. The compositions of claim 30, wherein the polymerization initiator system comprises an initiator selected from the group consisting of benzil diketones, DL-camphorquinone, peroxides, lauryl peroxide, tributyl hydroperoxide, cumene hydroperoxide, 1,1'-azobis (cyclohexanecarbonitrile), and benzoyl peroxide, and an accelerator selected from the group consisting of tertiary amines, dimethylaminoethyl methacrylate, diethylaminoethyl methacrylate, aromatic tertiary amines, 4-(N,N-dimethyl)aminobenzoate, dimethyl-p-toluidine, and dihydroxyethyl-p-toludine.

33. The compositions of claim 30, further comprising one or more of ultra-violet light absorbers, anti-oxidants, stabilizers, fillers, pigments, opacifiers, or handling agents.

34. The compositions of claim 33, wherein the filler is selected from the group consisting of amorphous silica, spherical silica, colloidal silica, barium glasses, quartz, ceramic fillers, silicate glass, hydroxyapatite, calcium carbonate, fluoroaluminosilicate, barium sulfate, quartz, barium silicate, strontium silicate, barium borosilicate, barium boroaluminosilicate, strontium borosilicate, strontium boroaluminosilicate, glass fibers, lithium silicate, ammoniated calcium phosphate, deammoniated calcium phosphate, alumina, zirconia, tin oxide, polymer powders, polymethyl methacrylate, polystyrene, and polyvinyl chloride, titania, and combinations thereof.

35. A dental luting cement or cavity filling material composition, comprising
about 5 wt. % to about 60 wt. % of a polymerizable component comprising at least one monomer or prepolymer selected from the group consisting of 2,2'-bis [4-(3-methacryloxy-2-hydroxy propoxy)-pheniyl]-propane, dipentaerythritol pentaacrylate. pentaerythritol dimethacrylate, the condensation product of ethoxylated bisphenol A and glycidyl methacrylate, the condensation product of 2 parts hydroxymethylmethacrylate and 1 part triethylene glycol bis(chlorofomate), and polyurethane dimethacrylates;
about 0.05 wt. % to about 5 wt. % of a polymerization initiator system;
about 40 wt. % to about 90 wt. % of a filler; and
an anti-microbial agent selected from the group consisting of salicylic acid, 4-amino salicylic acid, esters of salicylic acid, esters of 4-aminosalicylic acid, and sulfanilamide, in an amount of about 0.1 wt. % to about 5 wt. %, based on the total weight of the composition, wherein the water sorption of the cured luting cement or cavity filling material is less than about 50 $\mu g/mm^3/$week.

36. The compositions of claim 35, wherein the polymerizable component further comprises a component selected from the group consisting of hydroxyalkyl methacrylates, 2-hydroxyethyl methacrylate, 1,6-hexanediol dimethacrylate, 2-hydroxypropyl methacrylate, glyceryl dimethacrylate, ethyleneglycolmethacrylates, ethyleneglycol methacrylate, diethyleneglycol methacrylate, triethyleneglycol methacrylate, tetraethyleneglycol methacrylate, methacrylic acid, maleic acid p-vinylbenzoic acid, 11-methacryloyloxy-1,1-undecanedicarboxylic acid, 1,4-dimethacryloyloxyethylpyromellitic acid, 6-methacryloyloxyethylnaphthalene-1,2,6-tricarboxylic acid, 4-methacryloyloxyethyltrimellitic acid and the anhydride thereof, 4-methacryloyloxyethyltrimellitic acid and an anhydride thereof, 4-(2-hydroxy-3-methacryloyloxy) butyltrimellitic acid and an anhydride thereof, 2,3-bis(3,4-dicarboxybenzoyloxy)propyl methacrylate, methacryloyloxytyrosine, N-methacryloyloxytyrosine, N-methacryloyloxyphenylalanine, methacryloyl-p-aminobenzoic acid, the adduct of 2-hydroxyethyl methacrylate with pyromellitic dianhydride, the adduct of 2-hydroxyethyl methacrylate with maleic anhydride, the adduct of 2-hydroxyethyl methacrylate with 3,3', 4,4'-benzophenonetetracarboxylic dianhydride, the adduct of 2-hydroxyethyl methacrylate with 3,3',4,4'-biphenyltetracarboxylic dianliydride, the adduct of an aromatic dianhydride with an excess of 2-HEMA, the adduct of 2-HEMA with ethylene glycol bistrimellitate dianhydride, the adduct of 3,3',4,4'-diphenylsulfone tetracarboxylic dianhydride and 2-HEMA, the adduct of pyromellitic dianhydride with glycerol dimethacrylate, 2-methacryloyloxyethyl acidophosphate, 2-methacryloyloxypropyl acidophosphate, 4-methacryloyloxybutyl acidophosphate, 8-methacryloyloxyoctyl acidophosphate, 10-methacryloyloxydecyl acidophosphate, bis(2-methacryloyloxyethyl)acidophosphate, 2-methacryloyloxyethylphenyl acidophosphate, 2-sulfoethyl methacrylate, 3-sulfo-2-butyl methacrylate, 3-bromo-2-sulfo-2-propyl methacrylate, 3-methoxy-1-sulfo-2-propyl methacrylate, and 1,1-dimethyl-2-sulfoethyl methacrylamide.

37. The compositions of claim 35, wherein the polymerization initiator system comprises an initiator selected from the group consisting of benzil diketones, DL-camphorquinone, peroxides, lauryl peroxide, tributyl hydroperoxide, cumene hydroperoxide, 1,1'-azobis (cyclohexanecarbonitrile), and benzoyl peroxide, and an accelerator selected from the group consisting of tertiary amines, dimethylaminoethyl methacrylate, diethylaminoethyl methacrylate, aromatic tertiary amines, 4-(N,N-dimethyl)aminobenzoate, dimethyl-p-toluidine, and dihydroxyethyl-p-toluidine.

38. The compositions of claim 35, further comprising one or more of ultra-violet light absorbers, anti-oxidants, stabilizers, pigments, opacifiers, or handling agents.

39. The compositions of claim 35, wherein the filler is selected from the group consisting of amorphous silica, spherical silica, colloidal silica, barium glasses, quartz, ceramic fillers, silicate glass, hydroxyapatite, calcium carbonate, fluoroaluminosilicate, barium sulfate, quartz, barium silicate, strontium silicate, barium borosilicate, barium boroaluminosilicate, strontium borosilicate, strontium boroaluminosilicate, glass fibers, lithium silicate, ammoniated calcium phosphate, deammoniated calcium phosphate, alumina, zirconia, tin oxide, polymer powders, polymethyl methacrylate, polystyrene, and polyvinyl chloride, titania, and combinations thereof.

40. A dental luting cement or cavity filling material composition, comprising
  about 10 wt. % to about 40 wt. % of a polymerizable component comprising at least one monomer or prepolymer selected from the group consisting of 2,2'-bis [4-(3-metlacryloxy-2-hydroxy propoxy)-phenyl]-propane, dipentaerythritol pentaacrylate, pentaerythritol dimethacrylate, the condensation product of ethoxylated bisphenol A and glycidyl methacrylate, the condensation product of 2 parts hydroxymethylmethacrylate and 1 part triethylene glycol bis(chloroformate), and polyurethane dimethacrylates;
  about 0.05 wt. % to about 5 wt. % of a polymerization initiator system;
  about 40 wt. % to about 90 wt. % of a filler; and
  an anti-microbial agent selected from the group consisting of salicylic acid, 4-amino salicylic acid, esters of salicylic acid, esters of 4-aminosalicylic acid, and sulfanilamide, in an amount of about 0.1 wt. % to about 5 wt. %, based on the total weight of the composition, wherein the water sorption of the cured luting cement or cavity filling material is less than about 50 $\mu g/mm^3$/week.

41. The compositions of claim 40, wherein the polymerizable component further comprises a component selected from the group consisting of hydroxyalkyl methacrylates, 2-hydroxyethyl methacrylate, 1,6-hexanediol dimethacrylate, 2-hydroxypropyl methacrylate, glyceryl dimethacrylate, ethyleneglycolmethacrylates, ethyleneglycol methacrylate, diethyleneglycol methacrylate, triethyleneglycol methacrylate, tetraethyleneglycol methacrylate, methacrylic acid, maleic acid p-vinylbenzoic acid, 11-methacryloyloxy-1,1-undecanedicarboxylic acid, 1,4-dimethacryloyloxyethylpyromellitic acid, 6-methacryloyloxyethylnaphthalene-1,2,6-tricarboxylic acid, 4-methacryloyloxymethyltrimellitic acid and the anhydride thereof, 4-methacryloyloxyethyltrimellitic acid and an anhydride thereof, 4-(2-hydroxy-3-methacryloyloxy) butyltrimellitic acid and an anhydride thereof, 2,3-bis(3,4-dicarboxybenzoyloxy)propyl methacrylate, methacryloyloxytyrosine, methacryloyloxytyrosine, N-methacryloyloxyphenylalanine, methacryloyl-p-aminobenzoic acid, the adduct of 2-hydroxyethyl methacrylate with pyromellitic dianhydride, the adduct of 2-hydroxyethyl methacrylate with maleic anhydride, the adduct of 2-hydroxyethyl methacrylate with 3,3', 4,4'-benzophenonetetracarboxylic dianhydride, the adduct of 2-hydroxyethyl methacrylate with 3,3',4,4'-biphenyltetracarboxylic dianhydride, the adduct of an aromatic dianhydride with an excess of 2-HEMA, the adduct of 2-HEMA with ethylene glycol bistrimellitate dianhydride, the adduct of 3,3',4,4'-diphenylsulfone tetracarboxylic dianhydride and 2-HEMA, the adduct of pyromellitic dianhydride with glycerol dimethacrylate, 2-methacryloyloxyethyl acidophosphate, 2-methacryloyloxypropyl acidophosphate, 4-methacryloyloxybutyl acidophosphate, 8-methacryloyloxyoctyl acidophosphate, 10-methacryloyloxydecyl acidophosphate, bis(2-methacryloyloxyethyl)acidophosphate, 2-methacryloyloxyethylphenyl acidophosphate, 2-sulfoethyl methacrylate, 3-sulfo-2-butyl methacrylate, 3-bromo-2-sulfo-2-propyl methacrylate, 3-methoxy-1-sulfo-2-propyl methacrylate, and 1,1-dimethyl-2-sulfoethyl methacrylamide.

42. The compositions of claim 40, wherein the polymerization initiator system comprises an inhibitor selected from the group consisting of benzil diketones, DL-camphorquinone, peroxide, lauryl peroxide, tribuytl hydroperoxide, cumene hydroperoxide, 1,1'-azobis (cyclohexanecarbonitrile), and benzoyl peroxide, and an accelerator selected from the group consisting of tertiary amines, dimethylaminoethyl metharcrylate, diethylaminoethyl methacrylate, aromatic tertiary amines, 4-(N,N-dimethyl)aminobenzoate, dimethyl-p-toluidine, and dihydroxyethyl-p-toluidine.

43. The compositions of claim 40, further comprising one or more of ultr-violet light absorbers, anti-oxidants, stabilizers, pigments, opacifiers, or handling agents.

44. The dental restorative composition of claim 40, wherein the filler is selected from the group consisting of amorphous silica, spherical silica, colloidal silica, barium glasses, quartz, ceramic fillers, silicate glass, hydroxyapatite, calcium carbonate, fluoroaluminosilicate, barium sulfate, quartz, barium silicate, strontium silicate, barium borosilicate, barium boroalumnosilicate, strontium borosilicate, strontium boroaluminosilicate, glass fibers, lithium silicate, ammoniated calcium phosphate, deammoniated calcium phosphate, alumina, zirconia, tin oxide, polymer powders, polymethyl methacrylate, polystyrene, and polyvinyl chloride, titania, and combinations thereof.

45. A dental restoration comprising a cured dental restorative composition as in claim 21.

46. A dental restoration comprising a cured composition as in claim 30.

47. A dental restoration comprising a cured composition as in claim 35.

48. A dental restoration comprising a cured composition as in claim 40.

49. A method for restoring a tooth comprising:

preparing an area of a tooth to be restored;

applying the anti-microbial polymerizable dental composition of claim 21 to the area to be restored; and curing the anti-microbial composition.

50. A method for restoring a tooth comprising:

preparing an area of a tooth to be restored;

applying the anti-microbial polymerizable dental composition of claim 30 to the area to be restored; and curing the anti-microbial composition.

51. A method for restoring a tooth comprising:

preparing an area of a tooth to be restored;

applying the anti-microbial pulymerizablc dental composition of claim 35 to the area to be restored; and curing the anti-microbial composition.

52. A method for restoring a tooth comprising:

preparing an area of a tooth to be restored;

applying the anti-microbial polymerizable dental composition of claim 40 to the area to be restored; and curing the anti-microbial composition.

\* \* \* \* \*

UNITED STATES PATENT AND TRADEMARK OFFICE
CERTIFICATE OF CORRECTION

PATENT NO.   : 6,326,417 B1
DATED        : December 4, 2001
INVENTOR(S)  : Jia, Weitao It is certified that error appears in the above-identified patent and that said Letters Patent is hereby corrected as shown below:

Column 3,
Line 17, after "to" delete "Wakline" and insert therefor -- Waknine --.
Line 46, before "to" delete "menomers" and insert therefor -- monomer --.

Column 5,
Line 26, after "sulfate" delete "quartz".

Column 10,
Line 48, after "plate" delete "using," and insert therefor -- using --.
Line 60, after "zones" insert therefor -- were --.

Column 12,
Line 18, after "generated" delete "by".

Column 13,
Line 48, delete "of3" and insert therefor -- of 3 --.

Column 14,
Line 1, before "showed" delete "cyla.te" and insert therefor -- cylate --.
Line 61, delete "ethylenegLycolmethacrylates" and insert therefor
-- ethyleneglycolmethacrylate --.

Column 15,
Line 56, before "barium" delete "quartz".

Column 18,
Line 29, after "sulfate," delete "quartz".

Column 19,
Line 52, delete "p-toludine" and insert therefor -- p-toluidine --.
Line 60, before "sulfate," delete "quartz".

Column 20,
Line 12, delete "bis(chlorofomate" and insert therefor -- bis(chloroformate --.

Column 21,
Line 19, after "sulfate" delete "quartz".

UNITED STATES PATENT AND TRADEMARK OFFICE
CERTIFICATE OF CORRECTION

PATENT NO. : 6,326,417 B1
DATED : December 4, 2001
INVENTOR(S) : Jia, Weitao

It is certified that error appears in the above-identified patent and that said Letters Patent is hereby corrected as shown below:

Column 22,
Line 39, delete "metharcrylate" and insert therefor -- methacrylate --.
Line 44, after "of" delete "ultr-violet" and insert therefor -- ultra-violet --.
Line 51, after "sulfate" delete "quartz".

Signed and Sealed this

Thirtieth Day of August, 2005

JON W. DUDAS
*Director of the United States Patent and Trademark Office*